United States Patent
Kirkpatrick

(10) Patent No.: US 9,623,196 B2
(45) Date of Patent: Apr. 18, 2017

(54) SYSTEM AND METHOD FOR TRAPPING AIR BUBBLES

(75) Inventor: Gregg Rodne Kirkpatrick, San Diego, CA (US)

(73) Assignee: CAREFUSION 303, INC., San Diego, CA (US)

(*) Notice: Subject to any disclaimer, the term of this patent is extended or adjusted under 35 U.S.C. 154(b) by 1057 days.

(21) Appl. No.: 13/221,742

(22) Filed: Aug. 30, 2011

(65) Prior Publication Data

US 2013/0053774 A1  Feb. 28, 2013

(51) Int. Cl.
| | | |
|---|---|---|
| A61M 5/36 | (2006.01) | |
| A61M 5/165 | (2006.01) | |
| A61M 5/40 | (2006.01) | |
| A61M 5/38 | (2006.01) | |
| A61M 1/36 | (2006.01) | |
| A61M 1/16 | (2006.01) | |
| B01D 19/00 | (2006.01) | |

(52) U.S. Cl.
CPC ............ *A61M 5/36* (2013.01); *A61M 1/1658* (2013.01); *A61M 1/3627* (2013.01); *A61M 5/165* (2013.01); *A61M 5/365* (2013.01); *A61M 5/38* (2013.01); *A61M 5/40* (2013.01); *B01D 19/0057* (2013.01); *A61M 2206/16* (2013.01)

(58) Field of Classification Search
CPC ........ A61M 1/3627; A61M 5/36–5/40; A61M 2206/16; A61M 5/165; A61M 1/1658; B01D 19/0057
USPC .......................................................... 604/122
See application file for complete search history.

(56) References Cited

U.S. PATENT DOCUMENTS

| | | | | |
|---|---|---|---|---|
| 2,693,801 A | * | 11/1954 | Forcman ........................ | 604/147 |
| 4,116,646 A | * | 9/1978 | Edwards .............................. | 96/6 |
| 4,966,703 A | * | 10/1990 | Kalnins et al. ............ | 210/512.1 |
| 5,252,229 A | * | 10/1993 | Rojey ................ | B01D 17/0205 |
| | | | | 210/512.1 |
| 6,246,739 B1 | * | 6/2001 | Khorana ................ | B01D 45/16 |
| | | | | 376/293 |
| 6,827,862 B1 | * | 12/2004 | Brockhoff et al. ........... | 210/787 |
| 7,279,031 B1 | * | 10/2007 | Wright ............................ | 96/189 |
| 7,819,953 B2 | | 10/2010 | Andersson | |
| 8,235,943 B2 | * | 8/2012 | Breznock et al. ............ | 604/122 |
| 2006/0025725 A1 | | 2/2006 | Cassidy | |
| 2006/0032486 A1 | * | 2/2006 | Prasad ........................... | 123/572 |
| 2009/0107335 A1 | * | 4/2009 | Wilt et al. ....................... | 95/261 |
| 2009/0114582 A1 | * | 5/2009 | Grant et al. .................. | 210/175 |
| 2009/0133699 A1 | * | 5/2009 | Nalagatla et al. ....... | 128/205.27 |

(Continued)

FOREIGN PATENT DOCUMENTS

| | | |
|---|---|---|
| WO | WO-2009/045587 A1 | 4/2009 |
| WO | WO-2009/082548 A1 | 7/2009 |

(Continued)

*Primary Examiner* — Laura Bouchelle
*Assistant Examiner* — Anh Bui
(74) *Attorney, Agent, or Firm* — McDermott Will & Emery LLP

(57) ABSTRACT

An air trap is disclosed that includes a body having a sealed interior space with an inner wall, a center axis, and an inlet and an outlet on the center axis. The air trap also includes at least one projection disposed within the interior space and coupled to the inner wall. The at least one projection extends from the inner wall toward the center axis with an inner edge nearest to the center axis.

12 Claims, 5 Drawing Sheets

(56) References Cited

U.S. PATENT DOCUMENTS

2009/0173695 A1* 7/2009 Wieting et al. ............... 210/665
2010/0056975 A1* 3/2010 Dale et al. ................... 604/6.16

FOREIGN PATENT DOCUMENTS

WO    WO-2009/134282 A1   11/2009
WO    WO 2011077420 A1 *  6/2011  .............. A61M 5/36

* cited by examiner

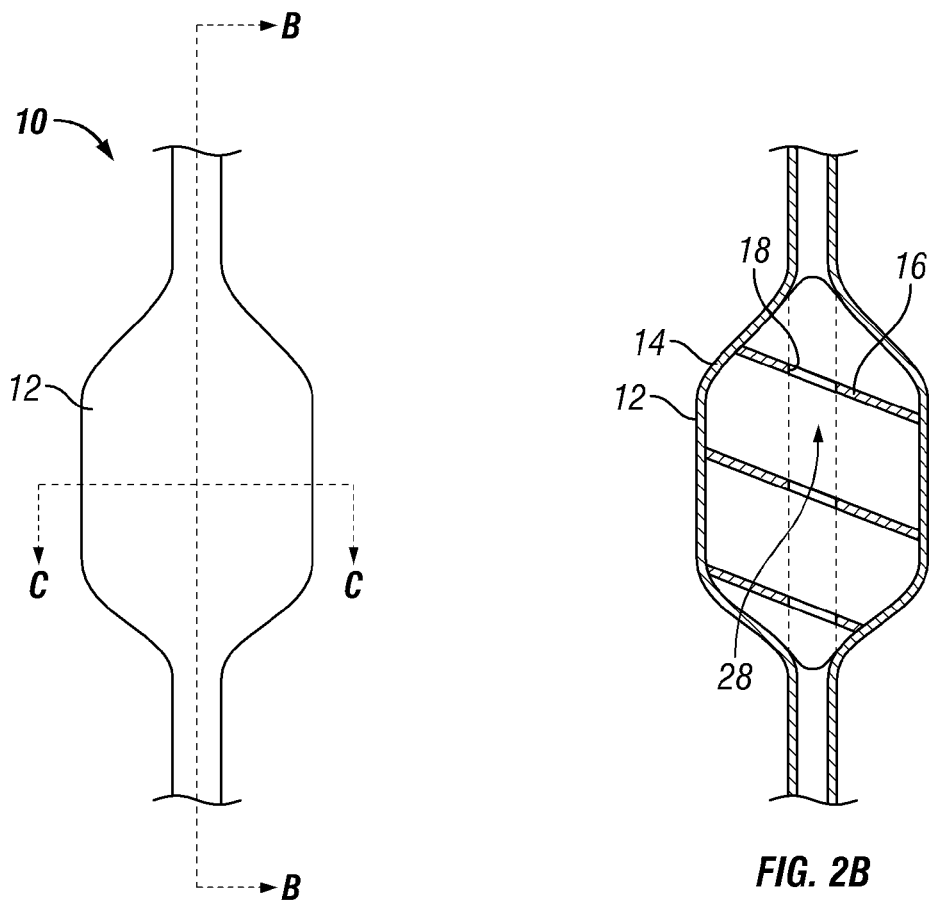
*FIG. 2A*
*FIG. 2B*
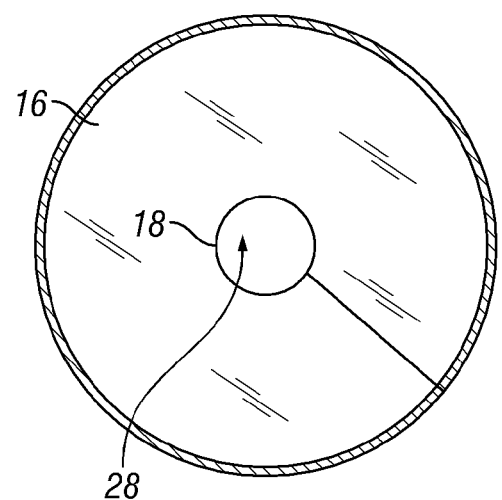
*FIG. 2C*

SYSTEM AND METHOD FOR TRAPPING AIR BUBBLES

BACKGROUND

Field

The present disclosure is related to trapping air bubbles that are entrained in a flow of liquid and, in particular, removing bubbles from intravenous (IV) lines.

Description of the Related Art

Patients in hospitals are often provided with medical fluids that are administered through an IV infusion. Air bubbles may be introduced into the medical fluid that is being administered through a number of mechanisms, including air in the lines or fittings when an IV set is first connected. Patients can accept a small amount of air introduced through an IV infusion without injury, especially if present as very small air bubbles as the gas will be absorbed from the blood. Large air bubbles, however, pose a risk if allowed to pass into the patient as a large bubble may block a small artery. While caregivers are usually diligent about flushing newly connected lines and ensuring that air is not injected into IV lines when administering medications, air bubbles are still sometimes present in the medical fluid being administered to the patient.

SUMMARY

It is desirable to provide a mechanism for trapping gas bubbles that may be entrained in the medical liquid passing through an IV line before it reaches the patient. The method and apparatus disclosed herein remove air bubbles from a liquid flowing through an IV line and retain the bubbles in an air trap.

In certain embodiments, an air trap is provided that includes a body having a sealed interior space with an inner wall, a center axis, and an inlet and an outlet on the center axis. The air trap also includes at least one projection disposed within the interior space and coupled to the inner wall. The at least one projection extends from the inner wall toward the center axis and has a inner edge nearest to the center axis.

In certain embodiments, an air trap is provided that includes a body having a sealed interior space with a cylindrical inner wall, a center axis, and an inlet and an outlet on the center axis. The air trap also includes a shelf disposed within the interior space and coupled to the inner wall. The shelf extends from the inner wall toward the center axis and has a inner edge nearest to the center axis.

In certain embodiments, an IV set is provided that includes an air trap having a body with a sealed interior space having an inner wall, a center axis, and an inlet and an outlet on the center axis. The air trap also includes at least one projection disposed within the interior space and coupled to the inner wall. The at least one projection extends from the inner wall toward the center axis and has a inner edge nearest to the center axis. The IV set also includes at least one fluid conduit coupled to one of the inlet and outlet of the air trap.

In certain embodiments, a method of removing gas bubbles from a flow of liquid is provided. The method includes the steps of allowing the liquid to flow through a conduit having a first cross-sectional area, and introducing the liquid from the conduit into an inlet of an air trap having an inner wall, a center axis, the inlet and an outlet on the center axis, and a second cross-sectional area that is at least 4× the first cross-sectional area. The air trap includes at least one projection disposed within the interior space and coupled to the inner wall. The at least one projection extends from the inner wall toward the center axis and has a inner edge nearest to the center axis. The air trap is oriented with the outlet above the inlet. The method also includes the step of allowing the gas bubbles to contact the projection.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 2A is an external view of the air trap of FIG. 1 according to certain aspects of the present disclosure.

FIGS. 2B-2C are cross-sections of the air trap of FIG. 1 according to certain aspects of the present disclosure.

DETAILED DESCRIPTION

The following description discloses embodiments of a system and method for removing air from a flowing liquid. In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. The systems and methods disclosed herein are discussed in the context of a medical fluid being administered to a patient via infusion in a healthcare facility. Nothing herein should be interpreted to limit the coverage of the claims to a healthcare environment or to medical treatment unless specifically stated as such.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Figure 1:
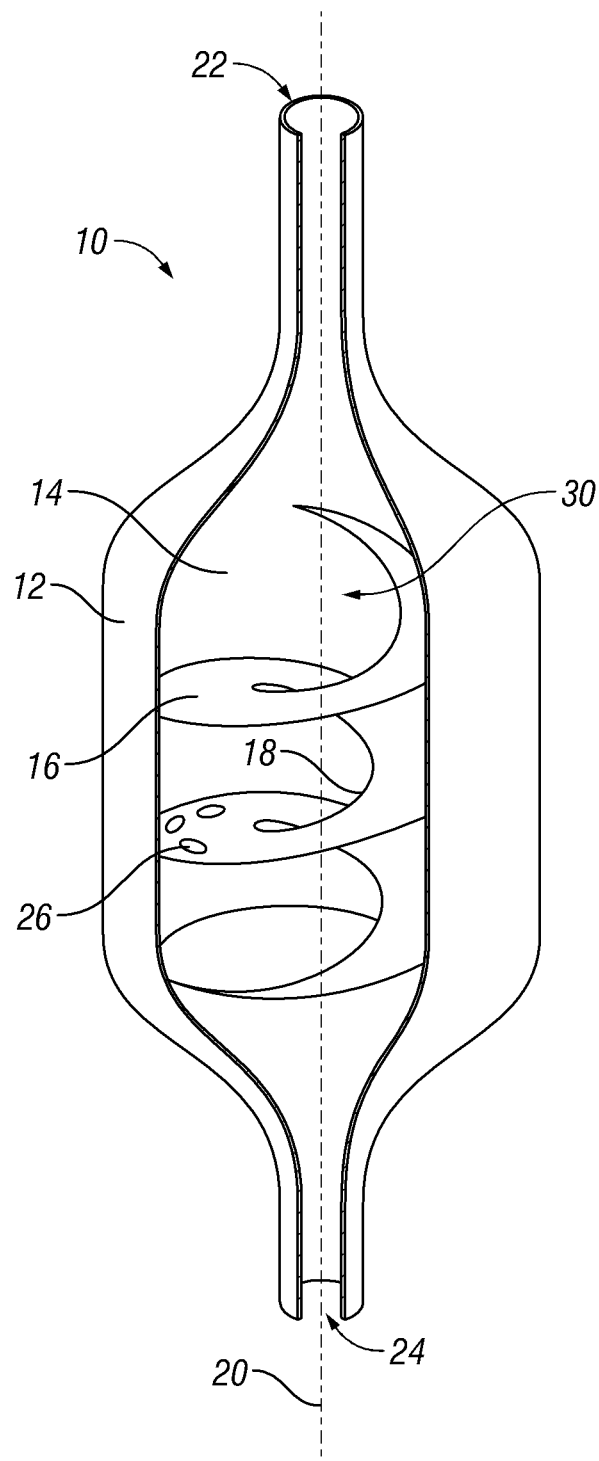
FIG. 1 is a cut-away view of an exemplary air trap according to certain aspects of the present disclosure.

FIG. 1 is a cut-away view of an exemplary air trap 10 according to certain aspects of the present disclosure. The air trap 10 comprises a body 12 having an inner wall 14, and an interior space 30. The interior space 30 has an inlet 24 and an outlet 22. In certain embodiments, the inlet 24 and the outlet 22 are positioned along the center axis. In certain embodiments, the outlet 22 is arranged over the inlet 24 as shown in FIG. 1. Within the interior space 30, there is a projection 16 that is coupled to the inner wall 14 and projects inward towards a center axis 20. In certain embodiments, the projection 16 is perpendicular to the inner wall 14. In certain embodiments, the projection 16 is angled with respect to the inner wall 14. In certain embodiments, the projection 16 forms one or more spirals around the inner wall 14. The projection 16 has an inner edge 18 that is, in certain embodiments, spaced away from the center axis 20. In certain embodiments, the inner edge 18 is spaced away from the center axis 20 by at least half the diameter of the inlet. In certain embodiments, the projection 16 has a plurality of holes 26, also referred to as "bubble gates," located over a portion of the projection 16.

In the embodiment of FIG. 1, the air trap 10 is a part of an IV set and arranged such that the medical fluid being delivered to the patient travels through the bubble trap 10. The medical fluid enters through the inlet 24 and travels upward through the interior space 30 to the outlet 22. The inlet 24 and outlet 22 will typically have the same inner diameter as the tubing of the IV set is typically a constant size. As the inner diameter of the body 12 is larger than the inner diameter of the inlet 22, the average upward fluid velocity of the medical fluid will slow as the medical fluid passes through the interior space 30 since the medical fluid spreads out to occupy the entire inner diameter. In certain embodiments, the inner diameter of the interior space 30 is twice (2×) the inner diameter of the inlet 24. In certain embodiments, the inner diameter of the interior space 30 is more than 3× the inner diameter of the inlet 24. As the medical fluid spreads out, however, the medical fluid passes into the spaces between the projections 52. As the medical fluid rises, the projections 52 will guide the flow into a spiral pattern following the projection 52. Bubbles in the flowing medical fluid will tend to rise until the bubbles contact the underside of the projection 52. Once the bubbles are in contact with the surface, the bubbles will tend to adhere to the surface through surface tension and remain stationary rather than continue to flow upward along the surface of the projection 52. In certain embodiments, the texture of the surface of the projection 16 is selected to increase the adhesion of bubbles that come into contact with the surface. In certain embodiments, the material of the projection 16 is chosen to increase the adhesion of bubbles to the surface of the projection according to the contact angle of a target fluid, such as saline solution, and the candidate material.

If the medical fluid contains a relatively large number of air bubbles, the air trap 10 may become partially filled with air such that the air trapping effectiveness is reduced. A caregiver may elect to remove the air trap 10, or the entire IV set that includes the air trap 10, and provide a new IV set with a fresh air trap 10. Alternatively, the caregiver may elect to flush the air trap by providing a vent path above the air trap, for example by shutting a valve in the attached tube that leads to the patient and opening a vent line connected through a Y-fitting, and agitating the air trap 10 to dislodge the trapped bubbles and cause the bubbles to flow out the outlet 22 and out the vent line. The caregiver may then return the air trap 10 to the original position and reestablish flow of the medical fluid to the patient.

FIG. 2A is an external view of the air trap 10 of FIG. 1 according to certain aspects of the present disclosure. FIG. 2A is an exterior view of the air trap 10 showing where cross-sections B-B and C-C have been taken through the body 12 and are shown in FIGS. 2B and 2C, respectively.

FIGS. 2B-2C are cross-sections of the air trap of FIG. 1 according to certain aspects of the present disclosure. FIG. 2B is a cross-section of the air trap 10 of FIG. 1 showing the body 12, the projection 16, and a clear flow path 28 passing through the projection 16. It can be seen that the projection 16 is formed as a spiral around the center axis 20 within the interior space 30. In certain embodiments, the projection 16 may also referred to as "shelf 16," as the projection 16 has a thickness that is much less than the length from the wall 14 to the edge 18.

FIG. 2C is the C-C cross-section from FIG. 2A of the air trap 10 of FIG. 1. In FIG. 2C, it can be seen how the inner edge 18 of projection 16 forms a perimeter of the clear flow path 28. In this embodiment, the clear flow path 28 passes from the inlet 24 to the outlet 22. In certain embodiments, the diameter of the clear flow path 28 is equal to the diameter of the inlet 24 which is the same as diameter of the outlet 22. In certain embodiments, the diameter of the clear flow path 28 is greater than the diameter of the inlet 24 and outlet 22.

Figure 3:
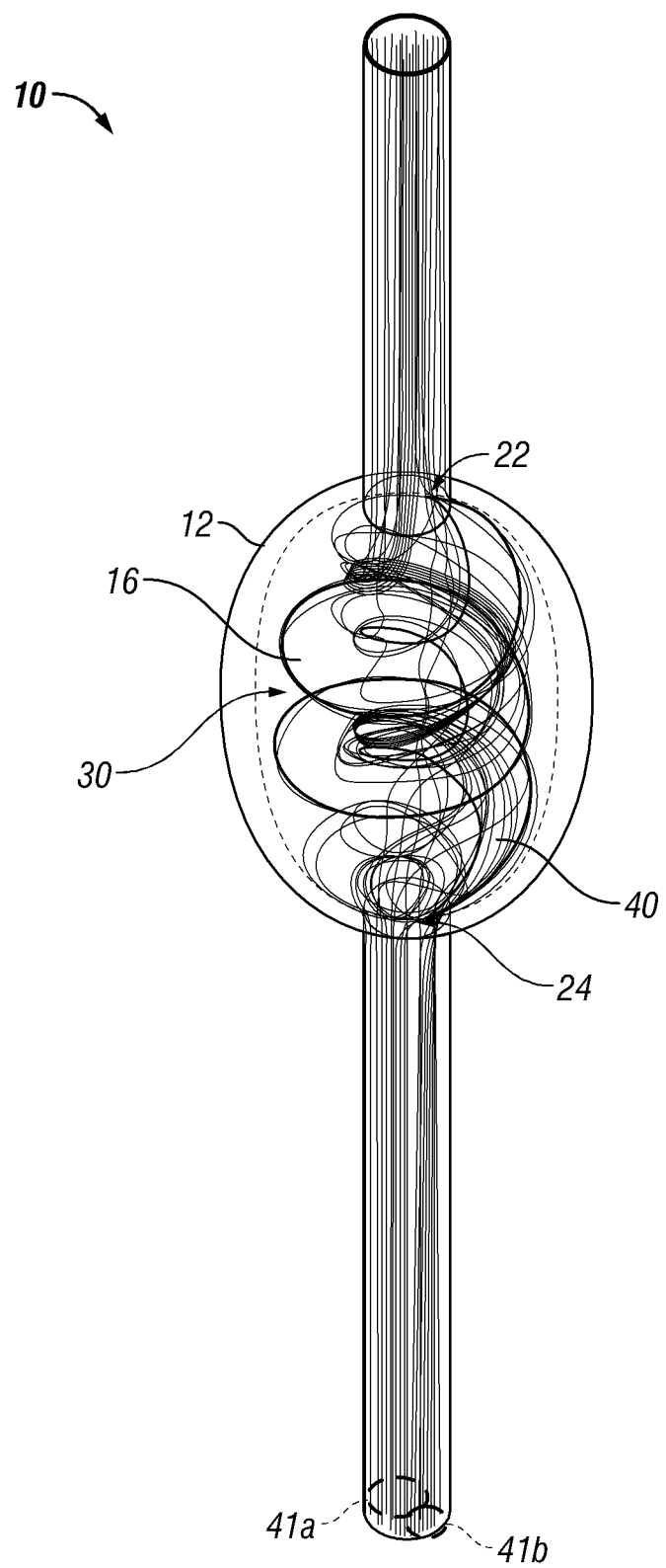
FIG. 3 is a perspective view of the air trap of FIG. 1 showing flow paths of bubbles according to certain aspects of the present disclosure.

FIG. 3 is a perspective view of the air trap 10 of FIG. 1 showing flow paths of bubbles according to certain aspects of the present disclosure. In this view, trajectories 40 trace the paths of a number of sample bubbles 41 as modeled by a fluid dynamics simulation. The sample bubbles 41 are positioned at various points at the inlet 24. It can be seen how bubbles 41b that are start near the walls of the inlet 24 pass into the spiral section of the projection 16, and their trajectories 40 follow the spiral one or more turns through the interior space 30. Bubbles 41a positioned at the center of inlet 24 can be seen to traverse the clear flow path 28 and travel essentially straight though the inner space 30 and out through outlet 22. In this simulation, adhesion of the bubbles 41 to the projection 16 was not modeled and therefore the bubbles 41a, 41b will all traverse the interior space 30 and exit through the outlet 22. In practice, however, there will be adhesion of air bubbles 41 to the surfaces of projection 16 such that the bubbles 41 will adhere and remain fixed at certain locations within the interior space 30. In this way, the bubbles 41 that contact the surface of projection 16 remain trapped within the air trap 10 and do not travel out outlet 22.

In embodiments comprising the holes 26, or bubble gates, bubbles 41 may pass through one of the projections 16 into a space above one projection 16 and below another aspect of projection 16. This allows bubbles 41 to migrate from area to area if an excess number of bubbles 41 accumulates in one portion of the air trap 10.

Figure 4:
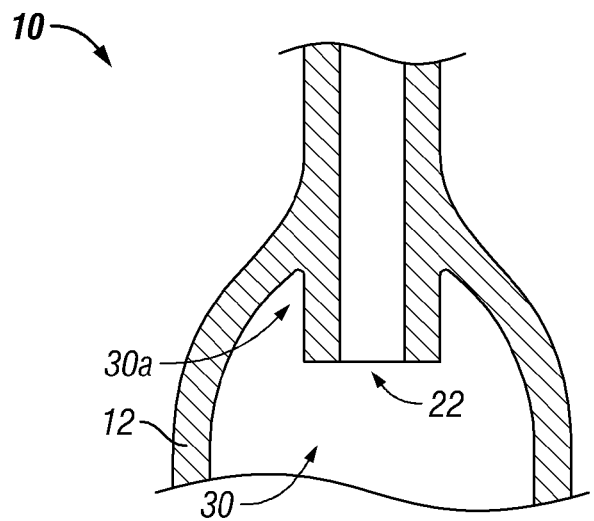
FIG. 4 is a cross-section view of a portion of another embodiment of an air trap according to certain aspects of the present disclosure.

FIG. 4 is a cross-section view of a portion of another embodiment of an air trap 10 according to certain aspects of the present disclosure. In this embodiment, the outlet 22 projects into the interior space 30 such that a portion 30a of the interior space 30 is above the outlet 22 when the air trap 10 is positioned such that the outlet 22 is directly over the inlet 24. This allows air bubbles 41 that are diverted to the outside of the projection 16 to pass upwards past the outlet 22 in the interior space 30 and accumulate in the portion 31a where the bubbles 41 will not be able to reach the outlet 22 itself, thereby preventing the air bubbles 41 from exiting the air trap 10.

Figure 5A:
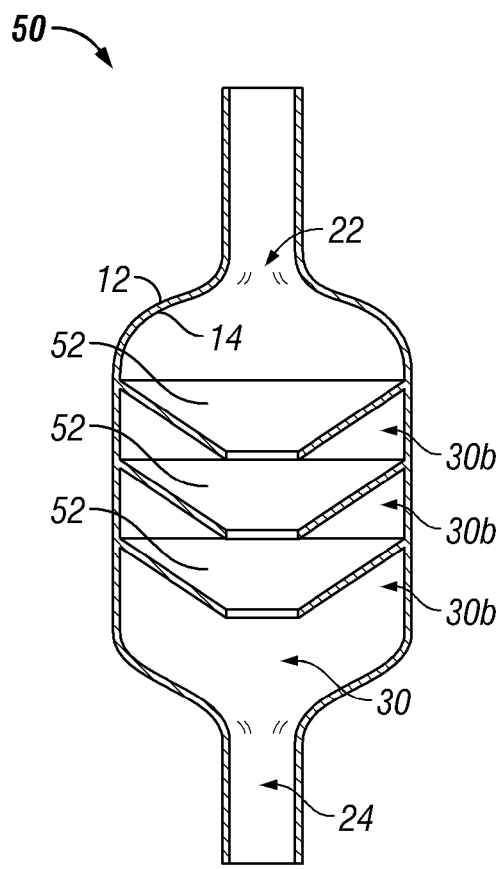
FIGS. 5A and 5B are cross-section and cut-away views, respectively, of another embodiment of an air trap according to certain aspects of the present disclosure.
Figure 5B:
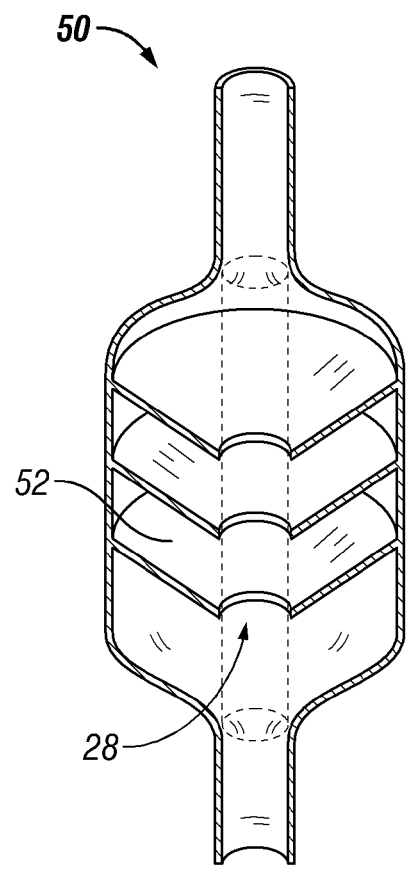

FIGS. 5A and 5B are cross-section and cut-away views, respectively, of another embodiment of an air trap 10 according to certain aspects of the present disclosure. It can be seen in FIG. 5A that there are a plurality of projections 52 that are shaped as truncated conical disks within the body 12. In certain embodiments, the projections 52 are flat disks.

Each projection 52 is coupled to the interior wall 14 along a horizontal plane through the body 12 when the outlet 22 is positioned over the outlet 24. The conical projection 52 has a central opening positioned on the center axis 20, such that a clear flow path 28 is formed through the sequential openings. It can be seen that the 3 projections 52 of the embodiment of FIG. 5A are positioned at equal spacings. In this embodiment, bubbles 41 that pass outside the opening in the center of projection 52 remain trapped in the spaces 30b between projections 52.

FIG. 5B is a perspective cut away view of the same embodiment of air trap 50 as shown in FIG. 5A, illustrating the conical nature and central opening of each of the projections 52. The dashed-line cylinder indicates the clear flow path 28 formed through the interior space 30 of the air trap 10. In certain embodiments, the cross-section area of the clear flow path, being a cross-section of the dashed-line cylinder, is greater than or equal to an area of the inlet.

Figure 6:
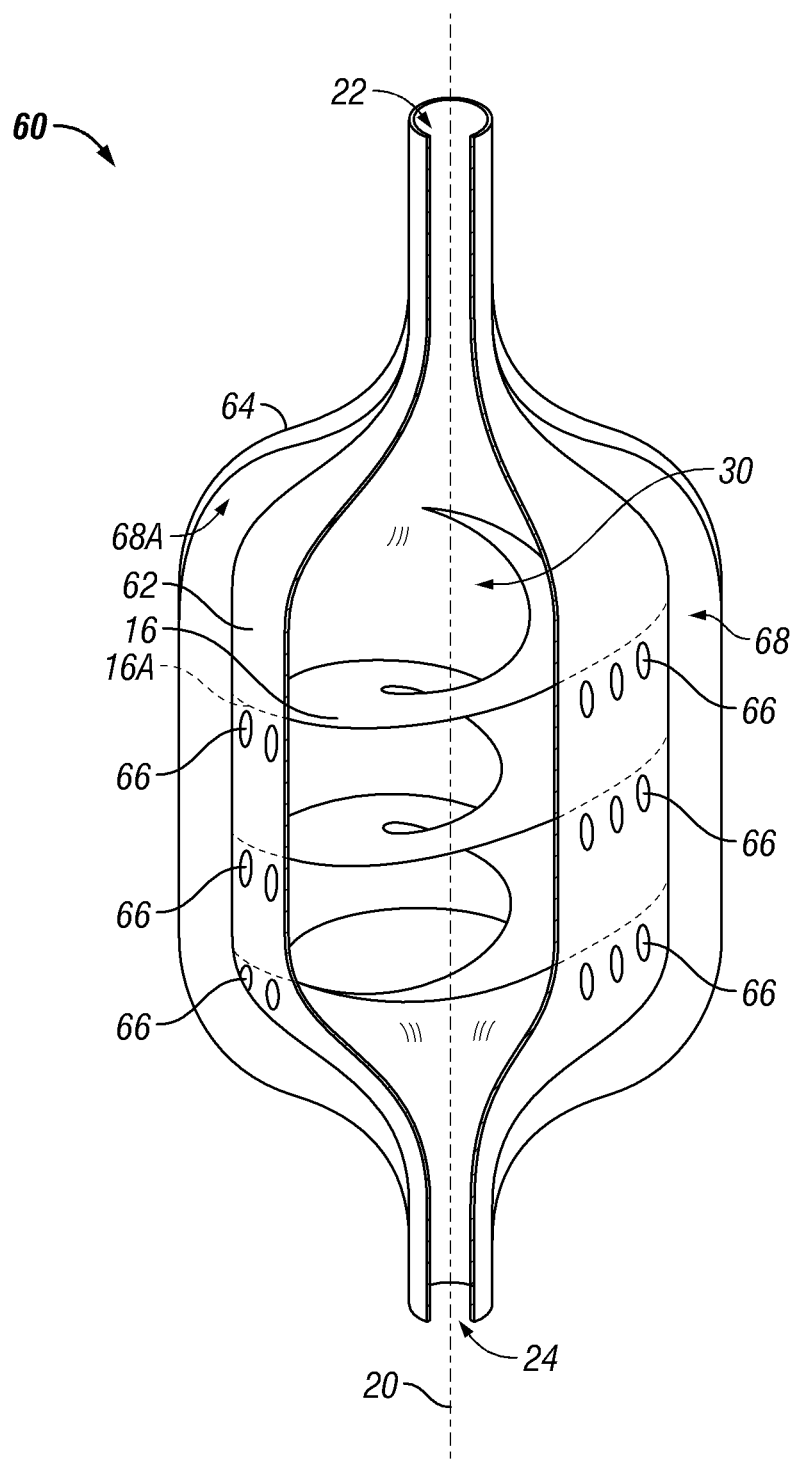
FIG. 6 is a cut-away view of another embodiment of an air trap according to certain aspects of the present disclosure.

FIG. 6 is a cut-away view of another embodiment of an air trap 60 according to certain aspects of the present disclosure. The air trap 60 has an inner shell 62 and an outer shell 64 that encloses the inner shell 62. The outer shell 64 is sealed around the inlet 24 and outlet 22 and is a part of the wetted volume of the air trap 60. The inner shell 62 comprises a plurality of passages 66 that allow air bubbles to pass from the interior space 30 into the intermediate space 68 between shells 62 and 64. The air bubbles that pass through the passages 66 will tend to rise into the volume 68A toward the outlet 22 and be trapped above the highest passages 66. In certain embodiments, the passages 66 are located just below the spiral lines 16A where the projection 16 contacts the inner shell 62. In certain embodiments, the passages 66 are evenly distributed over the inner shell 62. In certain embodiments, the passages 66 are slots. In certain embodiments, the passages 66 have flanges (not shown) that project into the intermediate space 68 to guide the bubbles away from the inner shell 62.

The disclosed air trap is configured to trap air bubbles entrained in a flow of fluid entering an inlet and passing through an interior space to an outlet. The interior space includes a projection that is coupled to an inner wall of the interior space and projects toward a center axis. An inner edge of the projection is spaced away from the center axis so as to provide a clear flow path from the inlet to the outlet. The projection traps air bubbles that contact the underside of the projection by surface tension.

It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims.

Reference to an element in the singular is not intended to mean "one and only one" unless specifically so stated, but rather "one or more." Unless specifically stated otherwise, the term "some" refers to one or more.

Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "operation for."

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. An air trap comprising:
   a body having a sealed interior space with an inner cylindrical wall, a center axis, and an inlet and an outlet on the center axis, wherein the inlet and outlet each have a diameter;
   a clear passage through the interior space that extends along the center axis from the inlet to the outlet, the clear passage having a diameter that is greater than or equal to the smaller of the inlet and outlet diameters; and
   at least one projection disposed within the interior space and coupled to the inner cylindrical wall, the at least one projection extending toward the central axis from the inner cylindrical wall to the clear passage and having a surface configured to substantially retain air bubbles on the surface, wherein the at least one projection comprises a spiral shelf having an inner edge, and wherein the inner edge is spaced away from the center axis along the entire length of the spiral shelf by a first gap, so that the inner edge defines a perimeter of the clear passage from the inlet to the outlet along the axis and wherein a portion of the inner cylindrical wall forms a hollow cylinder having, in cross-section, substantially straight parallel sides that extend in a direction along the central axis, for at least one complete rotation of the spiral shelf.

2. The air trap of claim 1, wherein the spiral shelf includes at least two complete rotations around the center axis.

3. The air trap of claim 1, wherein the at least one projection is configured to project inward at an angle to the center axis.

4. The air trap of claim 1, wherein:
   the diameters of the inlet and outlet are less than or equal to a first diameter;
   the interior space has a midpoint along the center axis between the inlet and outlet;
   the interior space has a second diameter at the midpoint; and
   the second diameter is equal to or larger than the first diameter.

5. The air trap of claim 4, wherein the second diameter is at least twice as long as the first diameter.

6. The air trap of claim 1, wherein the at least one projection comprises a plurality of holes through the projection each of the holes disposed between the inner wall and the clear passage.

7. The air trap of claim 1, wherein the outlet is disposed within the interior space such that, when the air trap is oriented with the outlet over the inlet, a portion of the interior space is above the outlet.

8. The air trap of claim 1, further comprising:
an outer shell surrounding the inner cylindrical wall; and
a plurality of passages through the inner cylindrical wall.

9. An air trap comprising:
a body having a sealed interior space with a cylindrical inner wall, a center axis, and an inlet and an outlet on the center axis;
a clear passage through the interior space that extends on the center axis from the inlet to the outlet; and
a plurality of shelves, each disposed within the interior space and coupled to the cylindrical inner wall, each shelf extending toward the center axis from the cylindrical inner wall to the clear passage and having an inner edge nearest to the clear passage, wherein a portion of the cylindrical inner wall forms a hollow cylinder having, in cross-section, substantially straight parallel sides that extend in a direction along the center axis, at least from one of the plurality of shelves to an adjacent one of the plurality of shelves.

10. An intravenous (IV) set comprising:
an air trap comprising:
a body having a sealed interior space with an inner cylindrical wall, a center axis, and an inlet and an outlet on the center axis; and
at least one projection disposed within the interior space and coupled to the inner cylindrical wall, the at least one projection extending toward the central axis from the inner cylindrical wall to a clear passage that extends through the interior space along the center axis, the at least one projection having an inner edge nearest to the clear passage, wherein the at least one projection comprises a spiral shelf having the inner edge, and wherein the inner edge is spaced away from the center axis along the entire length of the spiral shelf by a first gap, so that the inner edge defines a perimeter of the clear passage from the inlet to the outlet along the axis, wherein a portion of the inner cylindrical wall forms a hollow cylinder having, in cross-section, substantially straight parallel sides that extend in a direction along the central axis, for at least one complete rotation of the spiral shelf; and
at least one fluid conduit coupled to one of the inlet and outlet of the air trap.

11. The IV set of claim 10, wherein:
the at least one fluid conduit has a first inner diameter;
the interior space has a length and a midpoint along the center axis between the inlet and outlet;
the interior space has a second inner diameter at the midpoint;
the second inner diameter is at least twice as long as the first inner diameter.

12. The IV set of claim 11, wherein the spiral shelf includes at least two complete rotations around the center axis.

* * * * *